(12) United States Patent
McMichael

(10) Patent No.: US 7,666,178 B2
(45) Date of Patent: Feb. 23, 2010

(54) RETENTION DEVICE FOR MEDICAL COMPONENTS

(75) Inventor: Donald J. McMichael, South Jordan, UT (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 194 days.

(21) Appl. No.: 10/881,513

(22) Filed: Jun. 30, 2004

(65) Prior Publication Data

US 2006/0004345 A1  Jan. 5, 2006

(51) Int. Cl.
*A61M 25/00* (2006.01)
(52) U.S. Cl. ........................ 604/533; 604/523
(58) Field of Classification Search ............... 604/533, 604/910, 208, 905, 523
See application file for complete search history.

(56) References Cited

U.S. PATENT DOCUMENTS

| | | | |
|---|---|---|---|
| 3,613,497 A | 10/1971 | Heldermann | |
| 4,044,765 A | 8/1977 | Kline | |
| 4,296,949 A | 10/1981 | Muetterties et al. | |
| 4,322,194 A | 3/1982 | Einhorn | |
| 4,323,065 A | 4/1982 | Kling | |
| 4,367,995 A | 1/1983 | Mizusawa et al. | |
| 4,439,188 A | 3/1984 | Dennehey et al. | |
| 4,588,402 A | 5/1986 | Igari et al. | |
| 4,607,868 A | 8/1986 | Harvey et al. | |
| 4,639,019 A | 1/1987 | Mittleman | |
| 4,666,433 A | 5/1987 | Parks | |
| 4,685,901 A | 8/1987 | Parks | |
| 4,701,163 A | 10/1987 | Parks | |
| 4,798,592 A | 1/1989 | Parks | |
| 4,820,288 A | 4/1989 | Isono | |
| 4,929,236 A | 5/1990 | Sampson | |
| 4,969,879 A | * 11/1990 | Lichte | 604/533 |
| 5,047,021 A | 9/1991 | Utterberg | |
| 5,049,139 A | 9/1991 | Gilchrist | |
| 5,057,093 A | 10/1991 | Clegg et al. | |
| 5,080,650 A | 1/1992 | Hirsch et al. | |
| 5,104,157 A | 4/1992 | Bahner | |
| 5,230,332 A | 7/1993 | Strickland | |
| 5,233,979 A | 8/1993 | Strickland | |
| 5,234,417 A | 8/1993 | Parks et al. | |
| 5,242,389 A | 9/1993 | Schrader et al. | |
| 5,250,040 A | 10/1993 | Parks et al. | |
| 5,316,041 A | 5/1994 | Ramacier, Jr. et al. | |
| 5,336,203 A | 8/1994 | Goldhardt et al. | |
| 5,399,173 A | 3/1995 | Parks et al. | |
| 5,509,696 A | 4/1996 | Smith et al. | |

(Continued)

FOREIGN PATENT DOCUMENTS

AU    B88519/82    *    3/1983

(Continued)

*Primary Examiner*—Nicholas D Lucchesi
*Assistant Examiner*—Laura A Bouchelle
(74) *Attorney, Agent, or Firm*—Karl V. Sidor; Sue C. Watson; Scott B. Garrison

(57) ABSTRACT

The present invention is directed generally to an adapter for assist with the connection of a flexible tubing to a connector, and more particularly to a product that enables the flexible tubing to retain its ability to provide a secure connection even after multiple uses by resisting or limiting permanent deformation thereof.

3 Claims, 8 Drawing Sheets

U.S. PATENT DOCUMENTS

| | | |
|---|---|---|
| 5,694,922 A | 12/1997 | Palmer |
| 5,800,109 A | 9/1998 | Carruthers |
| 5,833,275 A | 11/1998 | Andersen |
| 5,836,924 A | 11/1998 | Kelliher et al. |
| 5,860,952 A | 1/1999 | Quinn |
| 5,860,960 A | 1/1999 | Quinn |
| 5,865,816 A | 2/1999 | Quinn |
| 5,891,113 A | 4/1999 | Quinn |
| 5,910,128 A | 6/1999 | Quinn |
| 5,984,378 A * | 11/1999 | Ostrander et al. ............ 285/319 |
| 6,036,673 A | 3/2000 | Quinn |
| 6,066,112 A * | 5/2000 | Quinn ..................... 604/93.01 |
| 6,419,670 B1 | 7/2002 | Dikeman |
| 6,464,686 B1 | 10/2002 | O'Hara et al. |
| 6,471,676 B1 | 10/2002 | DeLegge et al. |
| 6,722,705 B2 | 4/2004 | Korkor |
| 2003/0144647 A1 * | 7/2003 | Miyahara ..................... 604/523 |
| 2003/0153897 A1 | 8/2003 | Russo |
| 2004/0024381 A1 * | 2/2004 | Kurth et al. ................. 604/533 |
| 2004/0044330 A1 | 3/2004 | Li et al. |
| 2004/0111056 A1 | 6/2004 | Weststrate et al. |

FOREIGN PATENT DOCUMENTS

| | | |
|---|---|---|
| AU | 548262 | 12/1985 |
| FR | 67638 | 3/1958 |
| WO | WO 03/070151 | 8/2003 |
| WO | WO 2005/016221 | 2/2005 |

* cited by examiner

RETENTION DEVICE FOR MEDICAL COMPONENTS

BACKGROUND OF THE INVENTION

Enteral tubes for providing food and medication to a patient are well known. For example, U.S. Pat. No. 4,666,433, entitled Gastrostomy Feeding Device, invented by Parks and issued May 19, 1987; U.S. Pat. No. 4,701,163, entitled Gastrostomy Feeding Device, invented by Parks and issued Oct. 20, 1987; U.S. Pat. No. 4,798,592, entitled Gastrostomy Feeding Device, invented by Parks and issued Jan. 17, 1989; and U.S. Pat. No. 4,685,901, entitled Gastro-Jejunal Feeding Device, invented by Parks and issued Aug. 11, 1987 disclose earlier feeding tubes.

Referring to the illustrative drawing of FIG. 1A, there is shown a perspective view of an earlier enteral feeding device 20. The device 20 includes an elongated tubular member 51 formed from a stretchable elastomeric material such as silicone. FIG. 1B is an illustrative cross-sectional view of the tubular member 51 of the earlier device. The tubular member 51 defines a jejunal tube 22, a gastronomy tube 34 and a fluid line 46.

The jejunal feeding tube 22 (FIGS. 1A and 1B) includes an outlet end portion 24 (FIG. 1A) which can extend through a patient's stomach into the jejunum. The jejunal tube outlet end portion includes perforations 26 (FIG. 1A) which permit liquid food or medication to pass therethrough. The tube 22 (FIGS. 1A and 1B) is integrally connected to a jejunal tube inlet end portion 28 (FIG. 1A) which defines a jejunal inlet port 30 (FIG. 1A) having a removable plug cover 32 (FIG. 1A).

The gastrostomy tube 34 (FIG. 1A) is shorter than the jejunal tube 22 (FIGS. 1A and 1B) and includes a plurality of drainage inlets or food outlet ports such as inlet/outlet 36 (FIG. 1A). A gastrostomy tube end portion 37 (FIG. 1A) defines a gastrostomy inlet port 38 (FIG. 1A) having a plug cover 40 (FIG. 1A).

An inflatable balloon 42 is provided near the end of the gastrostomy tube 34 (FIGS. 1A and 1B) and is inflatable through a valve 44. The valve 44 is used to supply fluid to the balloon 42 through the fluid line 46 (FIGS. 1A and 1B).

Frictional contact between the elongated tubular member 51 (FIGS. 1A and 1B) and a locking ring 56 (FIG. 1A) is sufficiently great to prevent the tubular member 51 (FIGS. 1A and 1B) from moving further into the stomach. The locking ring 56 (FIG. 1A) remains in contact with a patient's abdominal wall during use. However, the frictional contact is sufficiently low to permit adjustment of placement of the tubular member 51 (FIGS. 1A and 1B) relative to a patient's abdomen.

Referring to the illustrative drawings of FIG. 2, there is shown a perspective view of an earlier device 20 in use. The inflated balloon 42 forms a gasket that seals the entrance to the stomach, and together with the locking ring 56, secures the device 20 in place.

While prior feeding tubes generally have been acceptable, there have been shortcomings with their use. In particular, for example, in order to provide food or medication to the jejunal inlet port 30 (FIG. 1A) of device 20 (FIG. 1A), a connector, such as a first connector 58 illustrated in FIG. 3 or a second connector 60 illustrated in FIG. 4, is inserted through the jejunal inlet port 30 (FIG. 1A). The inserted connector 58 (FIG. 3) or 60 (FIG. 4) is mechanically coupled to the jejunal inlet port 30 (FIG. 1A) and serves as a conduit between the jejunal tube 22 (FIGS. 1A and 1B) and an external feeding tube 62 or 64, shown in FIGS. 3 and 4 respectively. The external tube 62 or 64 is connected to a source of food such as a feeding bag (not shown).

In practice, connectors 58 or 60 such as those shown in FIGS. 3 and 4, for example, may be inserted into and removed from the jejunal inlet port 30 (FIG. 1A) or the gastrostomy inlet port 38 (FIG. 1A) numerous times during the course of use of the device 20 (FIGS. 1A and 2) which can be installed in a patient's stomach for extended periods of time. As mentioned above, the tubular member 51 (FIGS. 1A and 1B) which defines the jejunal tube inlet end 28 (FIG. 1A), and the gastrostomy tube end portion 37 (FIG. 1A) can be formed from a stretchable elastomeric material such as silicone. In order to produce an adequate mechanical coupling between the connector 58 (FIG. 3) or 60 (FIG. 4) and either the jejunal inlet port 30 (FIG. 1A) or the gastrostomy inlet port 38 (FIG. 1A), the connector is forced into place so as to produce a frictional engagement. Repeated insertions and removals of such connectors 58 (FIG. 3) or 60 (FIG. 4) can cause the jejunal inlet port 30 (FIG. 1A) or the gastrostomy inlet port 38 (FIG. 1A) to become somewhat stretched and deformed over time.

Unfortunately, as the jejunal and gastrostomy inlet ports 30, 38 (FIG. 1A) become more and more stretched in this manner, the tendency of a medical attendant responsible for coupling such a connector to the inlet ports 30, 38 often is to more forcibly push the connector into the jejunal or gastrostomy ports 30 or 38 resulting in still further stretching. Moreover, more force often must be exerted to dislodge a connector after such a forced insertion. Additionally, as the interior of the inlet ports 30, 38 becomes soiled with food oils, for example, an attendant may attempt to push a connector into the port even more forcibly-in order to compensate for the slipperiness of such oils, causing further deformation of the port opening.

The problem of achieving a tight fit between a jejunal or gastrostomy inlet port 30 or 38 (FIG. 1A) and such connectors 58 (FIG. 3) or 60 (FIG. 4), for example, has been exacerbated by the fact that in the past, such connectors often have been available in a variety of shapes and sizes. This variety will be apparent from the illustrative drawings of FIGS. 3 and 4 in which the first and second connectors 58, 60 have quite different shapes. Consequently, in the past it often has been desirable to construct jejunal or gastrostomy inlet ports, that can accommodate any of a variety of such differently shaped connectors. Unfortunately, such earlier inlet ports often could not readily accommodate such a variety of differently shaped connectors without the need to forcibly insert or forcibly remove the connectors.

Even with the advent of feeding tubes incorporating ferrules, the variety of connectors which are frequently used therewith can still lead to the forcing of the connector and the feeding tube together to make a secure connection. Depending on the tube and connector being used this forcing still may not be sufficient to create a connection which retains the connector in the tube so as to avoid an unintentional and/or undesired disconnection. Further, if sufficient force is applied during the connection of the prior connectors and tubes it may be such that the components are difficult to separate when desired. Such difficulties in separation may result in displacement of the feeding tube and/or discomfort to the patient during the attempted separation or even after the connector is ultimately separated from the tube.

These problems are only further exacerbated by the fact that it may be desired to use a certain type or brand of feeding device while the feeding bag or feeding set and the connector affixed thereto may be of a different brand and thus may not fit or connect with the feeding device as well as one specifically intended for use therewith. As a result a less desirable feeding device may be necessary in order to obtain the desired connection with the connector of the selected feeding set or a less desirable feeding solution in a feeding set having a connector which is compatible with the selected feeding device may be required to be selected for compatibility purposes.

Thus, there has been a need for a device to permit any of a variety of different shapes and sizes of connectors to be inserted into or removed from an inlet port of a feeding tube without the need to use excessive force and substantially without permanently deforming the feeding tube inlet port while still providing for the retention of the connector. The present invention meets these needs.

SUMMARY OF THE INVENTION

In response to the difficulties and problems discussed above, a receiving member adapted to assist with the connection of a tube and a connector has been developed. More specifically, one aspect of this invention is directed to a receiving member having a first end, an inner surface, an outer surface, and a plurality of fingers extending opposite the first end with the fingers being flexible. The receiving member being adapted to receive a connector associated with a feeding set. The fingers of the receiving member being adapted to deflect upon insertion of a connector therebetween so that the fingers may contact the connector in such a manner as to create an interface therebetween and upon removal of the connector the fingers adopt a shape at least substantially the same as that prior to insertion of the connector.

The present invention also contemplates an aspect which is directed to an adapter adapted for use with a tube, the adapter including a skeleton and a shell. The skeleton includes a first end, an inner surface, an outer surface, and a plurality of fingers extending opposite the first end, the fingers of the adapter being flexible. The shell contacts at least a portion of the outer surface of the skeleton. The skeleton is adapted to be received by or within the tube and is adapted to flex so that upon sufficient insertion of a connector the adapter contacts the connector in such a manner as to create an interface between the adapter and the connector and upon removal of the connector the fingers adopt a shape at least substantially the same as that prior to insertion of the connector. The skeleton is generally configured to urge the contours of the shell to interface with the connector when present so as to enhance retention of the connector within the adapter.

The present invention further contemplates an aspect which is directed to a relatively flexible enteral feeding tube for delivery of fluid to a patient's gastrointestinal tract. The enteral feeding tube has proximal and distal ends, and includes an enteral feeding lumen having a lumen inlet adjacent the proximal end of the tube and at least one lumen outlet adjacent the distal end of the tube. The lumen inlet is of sufficient size and is adapted to receive a feeding set connector. The lumen inlet further including an adapter and a coating, with the adapter having a first end, an inner surface, an outer surface, a plurality of fingers extending opposite the first end, where the fingers are flexible. The coating contacts at least a portion of the outer surface of the adapter and may form a shell in some aspects of the invention. The adapter is adapted to be received within or by a feeding tube and is adapted to flex so as upon insertion of the connector the adapter contacts the connector in such a manner as to create an interface between the adapter and the connector and upon removal of the connector the fingers adopt a shape at least substantially the same as that prior to insertion of the connector. As with other aspects of the present invention the adapter may be at least in part a skeleton.

A further aspect of the present invention relates to a receiving member adapted to assist with the connection of flexible tubing to a connector. The receiving member includes a first end, an inner surface, an outer surface, and a plurality of fingers extending opposite the first end. The fingers are flexible. The receiving member is adapted to receive a connector and the fingers of the receiving member are adapted to flex so that upon insertion of the connector therebetween, the fingers contact the connector in such a manner as to create an interface therewith and upon removal of the connector the fingers adopt a position at least substantially the same as that prior to insertion of the connector. As with other aspects of the present invention the receiving member is adapted to be positioned within the flexible tubing after the tubing is manufactured. Alternately, the receiving member may be at least partially encapsulated by the flexible tubing during manufacture of the tubing.

The invention will be more fully understood and further features and advantages will become apparent when reference is made to the following detailed description of exemplary aspects of the invention and the accompanying drawings.

BRIEF DESCRIPTION OF THE DRAWINGS

The purpose and advantages of the present invention will be apparent to those skilled in the art from the following detailed description in conjunction with the appended drawings in which.

DETAILED DESCRIPTION OF THE PRESENT INVENTION

The following detailed description will be made in the context of an adapter which is adapted for medical use. It is readily apparent, however, that the adapter would also be suitable for use with other types of systems, circuits or conduits and the like and is not intended to be limited to medical devices or use in a medical field. In addition, the invention will be described in the context of its various configurations. It should be appreciated that alternative arrangements of the invention can comprise any combination of such configurations. As such, the use of a desired aspect for ease in understanding and describing the invention shall not, in any manner, limit the scope of the invention.

Reference will now be made to the drawings in which the various elements of the present invention will be given numeral designations and in which the invention will be discussed so as to enable one skilled in the art to make and use the invention. It should be appreciated that each example is provided by way of explaining the invention, and not as a limitation of the invention. For example, features illustrated or described with respect to one aspect may be used with another aspect to yield still a further aspect. These and other modifications and variations are within the scope and spirit of the invention.

Figure 1A:
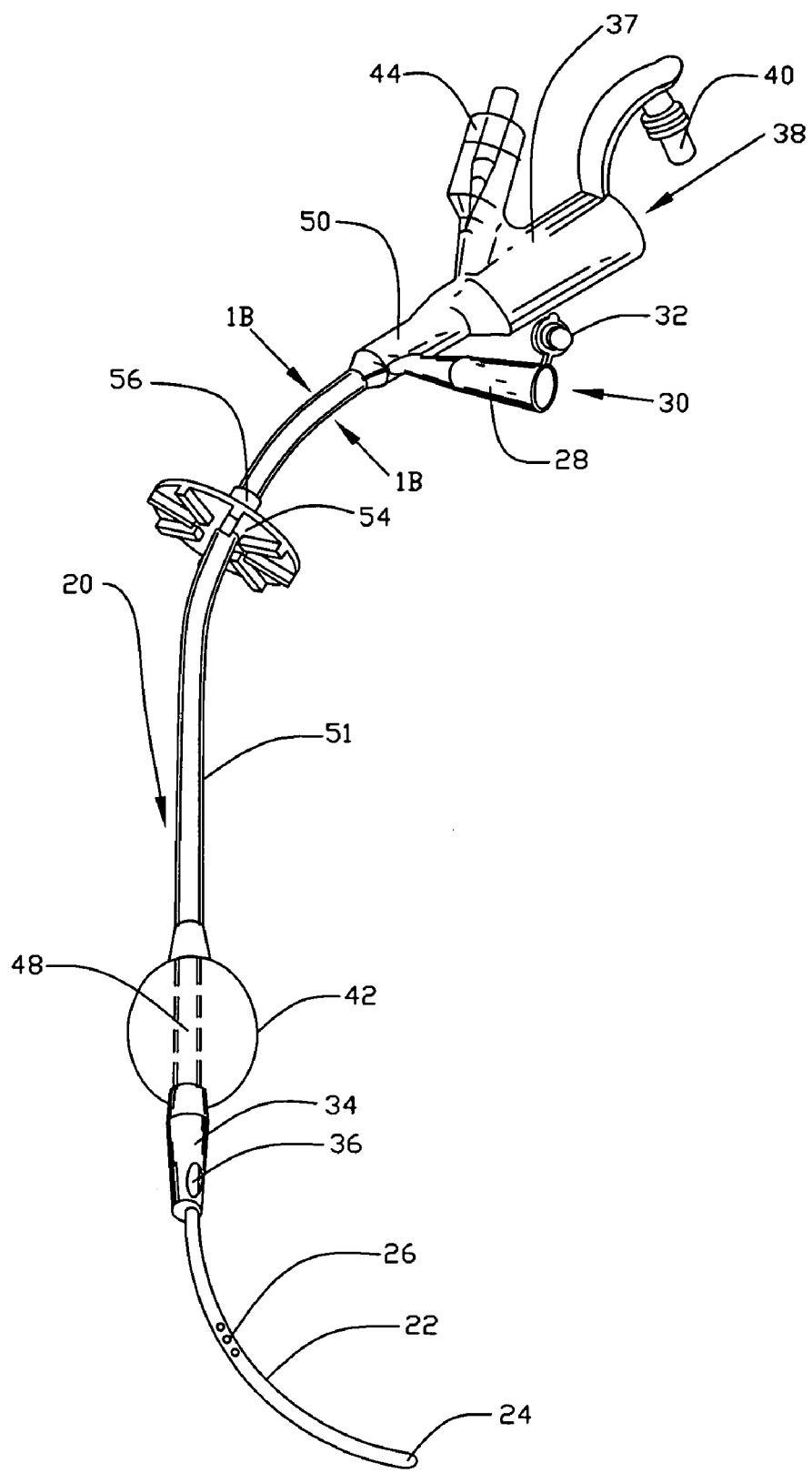
FIG. 1A is a perspective view of an earlier feeding tube.
Figure 1B:
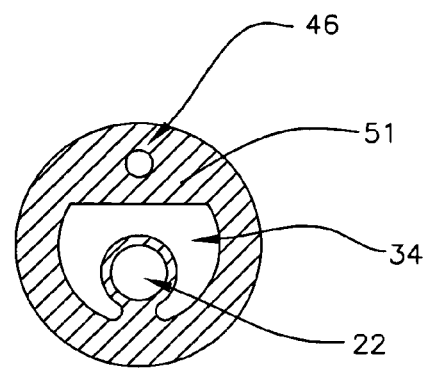
FIG. 1B is a cross-sectional view along line 1B-1B of FIG. 1A.
Figure 2:
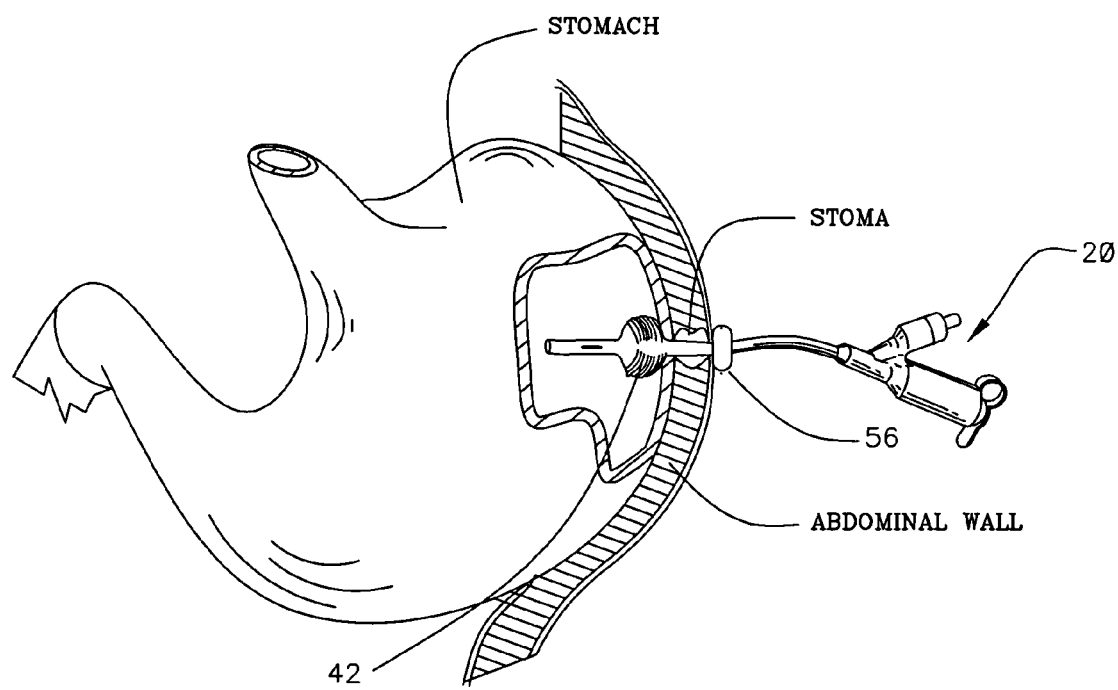
FIG. 2 is a perspective partially cutaway view of an earlier feeding tube installed in a patient.
Figure 3:
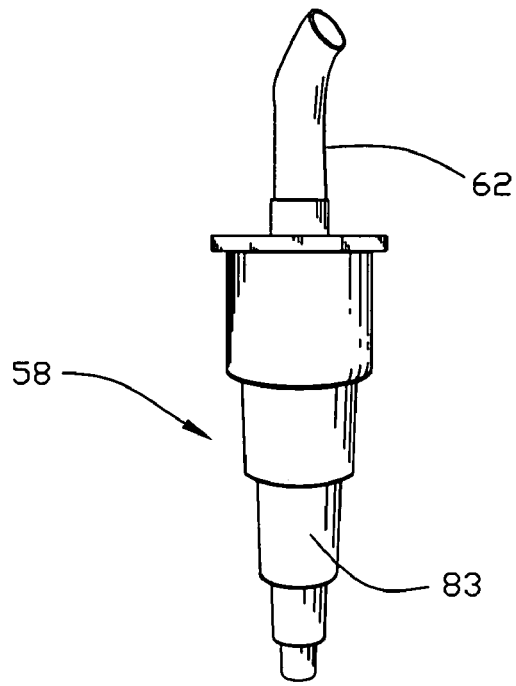
FIGS. 3 and 4 are side elevation views of earlier connectors for insertion into end portions of a feeding tube.
Figure 4:
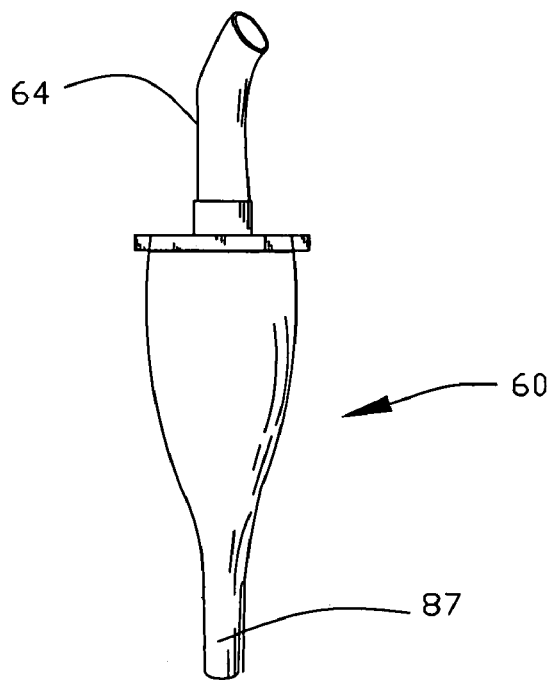
Figure 5:
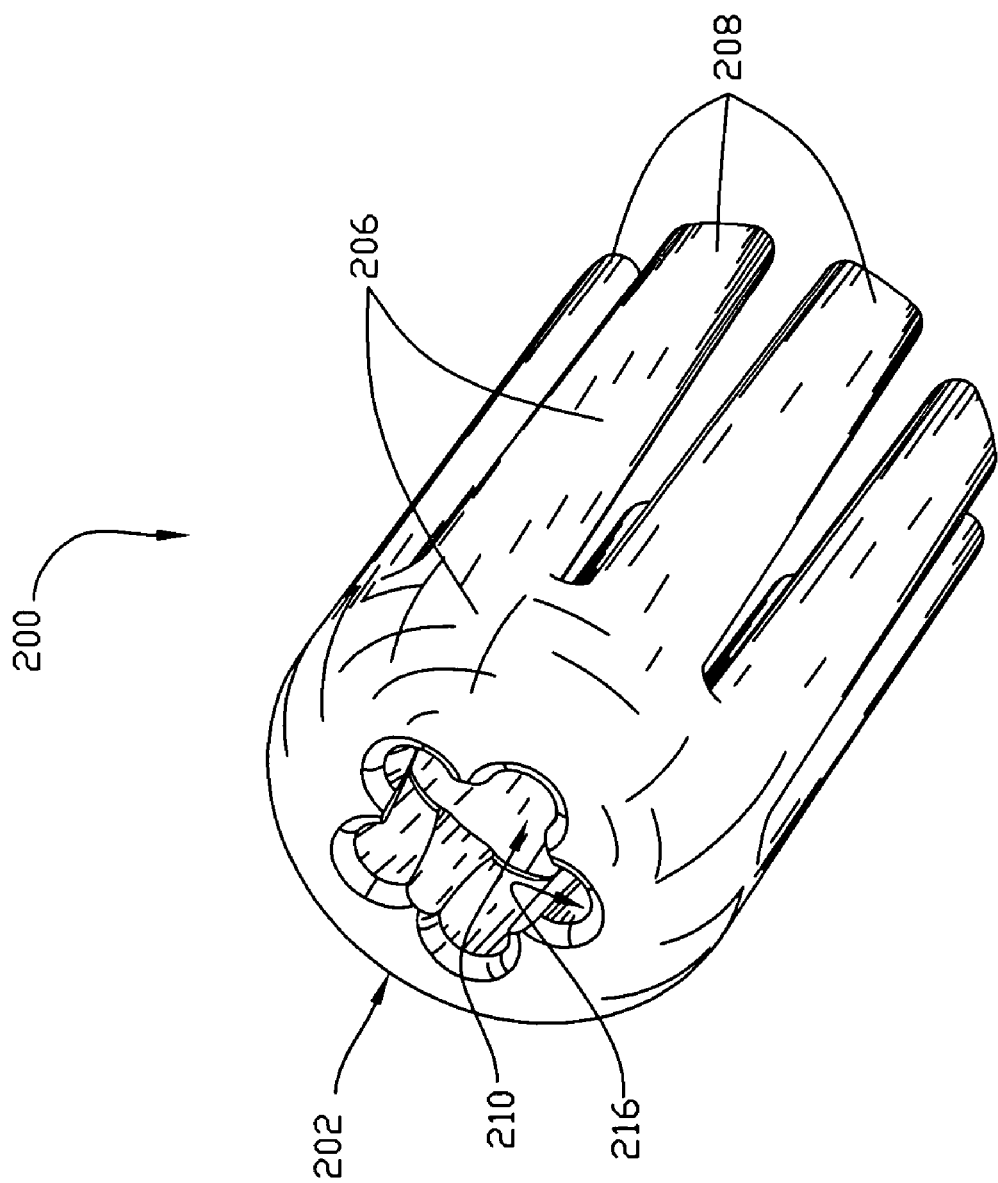
FIG. 5 is a perspective view of an adapter in accordance with the present invention.
Figure 6:
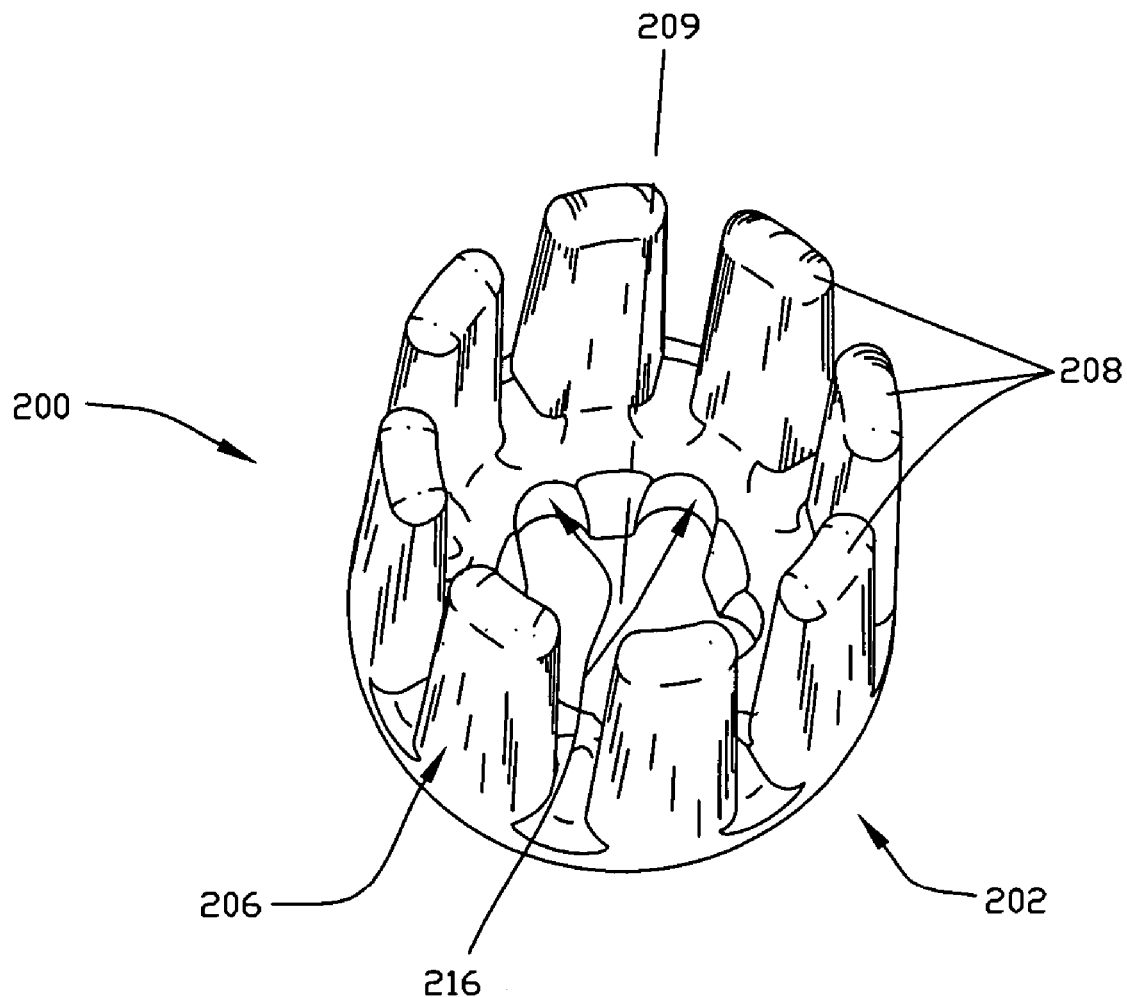
FIG. 6 is an alternate view of the adapter of FIG. 5.

Turning now to the drawings, and FIGS. 5 and 6 in particular, there is illustrated a perspective view of an aspect of an adapter or receiving member 200 in accordance with the present invention which may be inserted into the proximal end of a flexible tube or the like to assist with the retention of a connector which may be inserted into the proximal end of the tube to promote connection therebetween and the conduction of fluids therethrough.

Although, as discussed in more detail herein, the adapter may be in a variety of sizes and shapes, the adapters 200 shown in FIGS. 5-9 are merely exemplary and are illustrated as such for purposes of discussion and understanding. It will be appreciated that the size and shape of the adapter 200 may be dictated in part by the device or component the adapter 200 is intended to be used with and/or the size and shape of the skeleton therein, when present.

As illustrated in FIGS. 5 and 6, adapter 200 has a first end or base 202, an inner surface 204 (FIG. 6), an outer surface 206, and a plurality of fingers 208 extending opposite the first end. The first end or base 202 of the adapter 200 may be flat or rounded as illustrated and may be of any suitable size depending on the device or component it is intended to be used therewith. The adapter is adapted to receive a feeding set or at least a portion thereof including, for example, a portion of a connector which may be either permanently or temporarily affixed to the feeding set and which is adapted for communication between a feeding set and a feeding tube. The fingers 208 of the adapter 200 are intended to allow for radial expansion relative to the center axis 209 (FIG. 6) of the adapter 200 upon insertion of a portion of a feeding set connector (e.g., connectors 58, 60, and 61 in FIGS. 3, 4, and 7-8, respectively) or the like. The fingers 208 are intended to radially flex or deflect outwardly upon insertion of a feeding set connector or the like. Depending on the size and shape of the connector inserted therein the extent of expansion or deflection of the fingers 208 will vary. The fingers 208 are designed and constructed of such material or materials, including for example a memory material, such that once the connector is inserted as far as the adapter 200 will allow or as far as a clinician desires and the fingers are flexed or deflected outwardly, the fingers 208 will exert a radially inward force relative to the center axis 209 (FIG. 6) of the adapter 200. The radially inward force causes the fingers 208 to act on the connector. The inward force will act upon the connector in such a way so as to assist in the retention of the connector relative to the adapter 200 or any other device or component the adapter may be present in. The inward force will continue to be exerted until the object inserted into the adapter causing it to deform or deflect is removed therefrom at least until the point that the adapter 200 is no longer deformed or deflected. It is intended the fingers 208 of the adapter 200 be such that they are able to return to their original shape or adopt a shape substantially the same as that prior to insertion once the object causing the deflection or deformation is removed therefrom. The ability of the fingers to return to the same position or substantially the same position as that prior to insertion of the inserted object (e.g., connector) is contemplated even after numerous and/or prolonged expansions deflections thereof.

Benefits associated with the "memory" ability of the adapter and/or fingers and how it may be translated to the material in contact with or about the adapter and/or fingers is discussed in more detail below. Generally speaking, the ability of the fingers 208 and/or the adapter to return to the same or substantially the same position should be less than several minutes and is desirably less than one second.

Further with respect to the fingers 208 of the adapter 200, the fingers may take any number of suitable shapes and lengths. Any combination of suitable shapes and lengths is contemplated provided the particular combination is adapted to perform the above described functions of the fingers. Suitable finger shapes may be rounded, flat on one or more sides, tapered, and/or contoured.

As will be appreciated there are number of suitable materials or combinations thereof which may be used to form the adapter 200. Any such suitable material may be used. Exemplary suitable materials include silicone, polyurethane, PVC, polyetheramide, polycarbonate, nylon, polyethersulfone, etc., and combinations thereof. It will be appreciated that where the adapter or a portion thereof is made of the same material as the device or portion thereof into which it is positioned that the adapter will be of a higher durometer so as to be able to provide effects described herein. The opening may be sized and/or shaped to allow for overmolding as discussed in more detail below.

As will be appreciated the first end 202 of the adapter 200 will have an opening or aperture 210 therethrough which allows for fluids such as nutritional supplements and the like to pass therethrough. As suggested in FIG. 8, it will also be recognized that depending on the length of the connector 61 or the like being used in conjunction with the adapter 200, the distal end of the connector 61 may in some instances extend through the opening 210 (not shown in FIG. 8). While generally round in shape, the opening 210 may take any number of various shapes, including for example that shown in FIGS. 5 and 6. As noted above, in those instances where the distal end of the connector 61 extends through the first end 202 of the adapter 200, the opening 210 may be shaped so receive and/or grip the outer surface of the connector 61 being passed therethrough.

Another feature which may be present in one or more aspects of the present invention is a locking mechanism. A locking mechanism may assist with retention of a connector or the like within the adapter 200 and/or the component or device the adapter 200 is being used with. It will be appreciated that while reference is made a locking mechanism, it is understood that in some aspects of the present invention only a portion of the locking mechanism may be associated with the present invention and that the portion of the locking mechanism associated with the present invention may need to work with another portion of the mechanism associated with a connector or other inserted member in order to achieve the desired locking abilities. Nevertheless, the term locking mechanism will be used herein to refer to the portion thereof, if not the entire mechanism, which is associated with an adapter of the present invention.

The locking mechanism may be part of the first end 202 of the adapter 200. A variety of locking mechanisms may be used to insure a tight fit with certain connectors. The locking mechanism may simply be a friction fit enabled by contact between a connector and the inner wall 216 of the opening 210 in the first end 202 of the adapter 200. Alternately, a locking mechanism of a different variety may be more appropriate and/or necessary to insure a tight fit with certain connectors such as those having a protrusion or bayonet member. One suitable locking mechanism (not shown) may include a recess adapted to receive such a bayonet member, which upon insertion of the bayonet member into the recess may be rotated off-axis from the recess so that the connector may not be removed from the adapter until the bayonet member is realigned with the first recess. Another exemplary locking mechanism may include a boss and detent, where the adapter has either the boss or the detent and the connector has the other. Any suitable locking mechanism is contemplated by the present invention.

Having generally described the adapter 200 of the present invention, it will be appreciated that an adapter of the present invention may be included in a number of different components or devices. As noted above, one such exemplary device is a feeding tube or medical catheter. Although the adapter may be used with any of the proximal openings of the feeding tube, in the aspects of the present invention illustrated in the figures, the adapters are only illustrated in or about those proximal openings through which nutritional supplements and the like are intended to pass.

Figure 7:
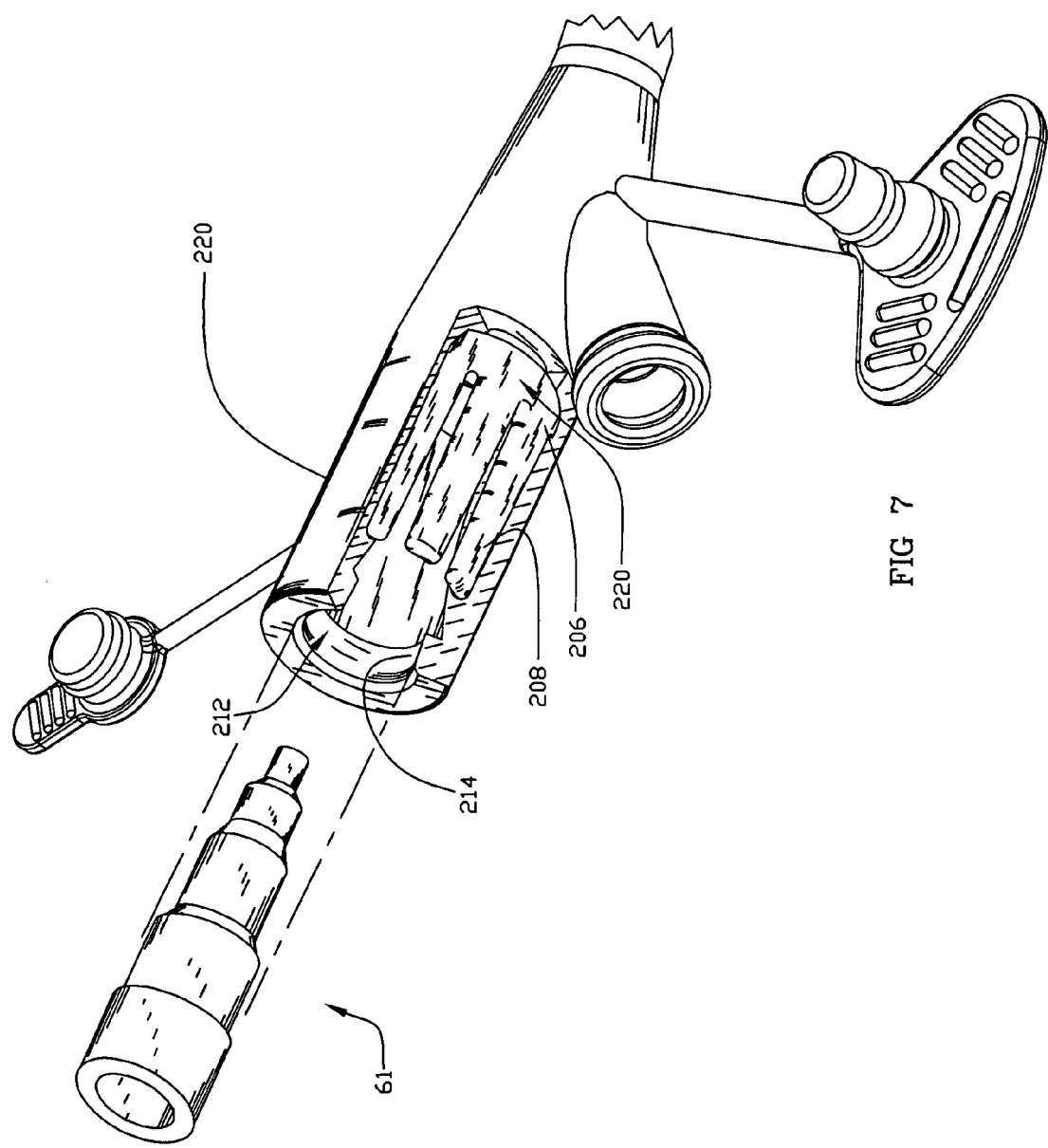
FIG. 7 is an elevational partially cut away side view of an adapter in accordance with the invention shown in an expanded or exploded view with a second member, the adapter being within an inlet of a flexible tube.
Figure 8:
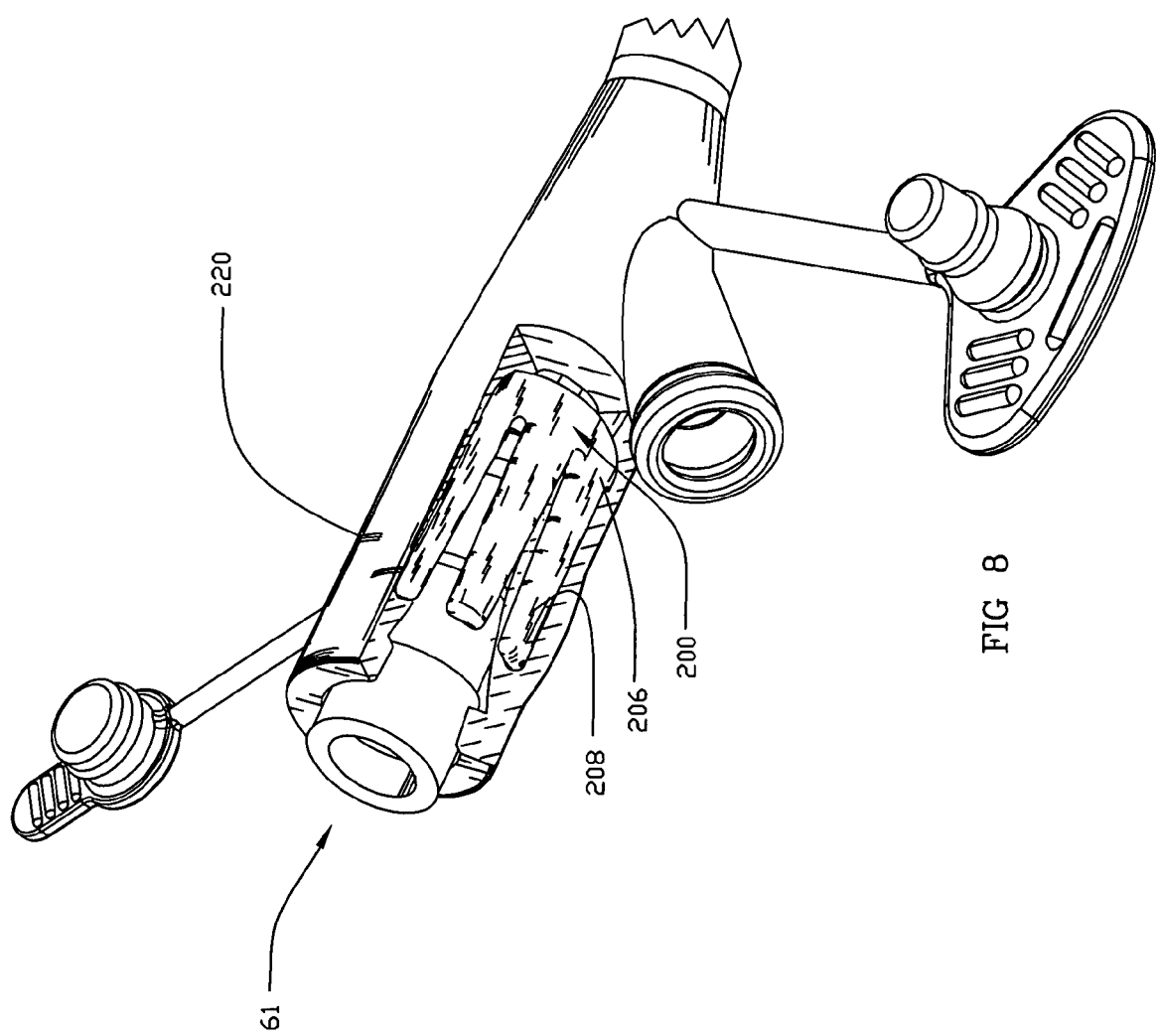
FIG. 8 is a side elevational view of the adapter of FIG. 7 having a connector interconnected therewith.

Referring to FIGS. 7 and 8 there is shown a portion of an exemplary feeding tube 220 having an adapter of the type described above inserted into the proximal feeding inlet opening 212. As shown in FIGS. 7 and 8, the adapter 200 can be surrounded by or included within a particular device or component, in this case a feeding tube 220. As will be appreciated, where the adapter 200 is at least partially overmolded or otherwise made into a device or component (e.g., where a component is formed about or substantially about the adapter or a portion thereof) post-manufacture inclusion may not be practical or possible.

Although shown in FIGS. 7 and 8 as being overmolded by the material of the feeding tube 220, it is also contemplated that an adapter 200 of the type described herein, for example, could be secured to or within the feeding tube by way of a friction fit within the feeding inlet opening 212, a glue or other adhesive and/or at least partially overmolding thereof. Furthermore, the present invention contemplates when the adapter 200 is positioned on the inside edge 214 of the feeding inlet opening 212, that the adapter may be placed in the opening 212 at the time of manufacture or at any post-manufacture time including up to the time of use by a clinician or other end user.

Whether encased within a device or component or merely secured or mounted to the surface thereof, the adapter of the present invention will act upon an object inserted therein in a similar fashion. That is, the adapter will operate in the same fashion, the only difference being whether the adapter 200 or portion thereof acts directly or indirectly upon the object inserted therein. That is, where the adapter 200 is to be in direct contact with the inserted object, it may be desirable for the fingers 208 thereof to be contoured or have a particular surface texture; whereas, when another material (e.g., an overmold) is between the adapter 200 and the inserted object, and the intermediary material is to be in direct contact with the inserted object, it may be desirable for the intermediary material to be contoured or have a particular surface texture to enhance the gripping or retention ability of the device or component. Furthermore, as a number of connectors have a plurality of contours and/or surfaces, it may be desirable for a portion of the shell and/or a portion of a coated or an overmolded surface about at least a portion of the adapter 200 to have a plurality of contours which are adapted to interface with one or more surfaces of the adapters. Therefore, rather than the adapter interfacing directly with the object inserted therein, where an intermediary material such as a shell and/or a coating or an overmold about at least a portion of the skeleton is between the adapter and the inserted object, the adapter will act upon the intermediary material to urge an interface between the inserted object and the intermediary material to promote better retention of the inserted object within the device or component in which the adapter is present until desired removal of the inserted object as well as to promote or create a better seal therebetween. Even though the adapter or the fingers of the adapter may not actually contact a connector because of an intermediary material, it is contemplated that where the adapter or fingers of the adapter urge the intermediary material to contact the connector or promote an interface therebetween that limitations directed to the adapter or fingers thereof contacting the connector shall be considered met.

Having generally described the concept of the adapters or retention members of the present invention, the disclosure now turns to some exemplary aspects of the present invention. In at least one aspect of the present invention, the adapter will include a skeleton. The skeleton is frequently used to provide strength and/or a structured "backbone" to the adapter and is frequently at least partially surrounded by a shell. That is the skeleton may be used to form the core of the adapter. By selecting the materials which comprise the skeleton from those which exhibit desirable qualities, one is able to obtain an adapter having certain flexibility, resiliency, and/or other features. While any suitable material or materials may be used to form the skeleton, exemplary materials include silicone, PVC, polyurethane, polyetheramide, polycarbonate, RADEL A or RADEL R (polyethersulfones available from Solvay Advanced Polymers), and nylon. At least one aspect of the present invention exemplarily include ULTEM, a polyetheramide available from GE Plastics.

In use the adapter is designed such that when flexed or deformed, it will attempt to return to its original non-flexed or non-deformed state. In doing so, whether secured to or overmolded within a flexible tube or the like, an adapter of the present invention is intended to reduce or prevent the flexible material of the devices or components with or in which it is used from becoming stretched out or permanently deformed such that their ability to retain a connector inserted therein remains substantially that of which they originally possessed at the later of the time of manufacture or the time at which the adapter or receiving member was inserted therein.

Figure 9:
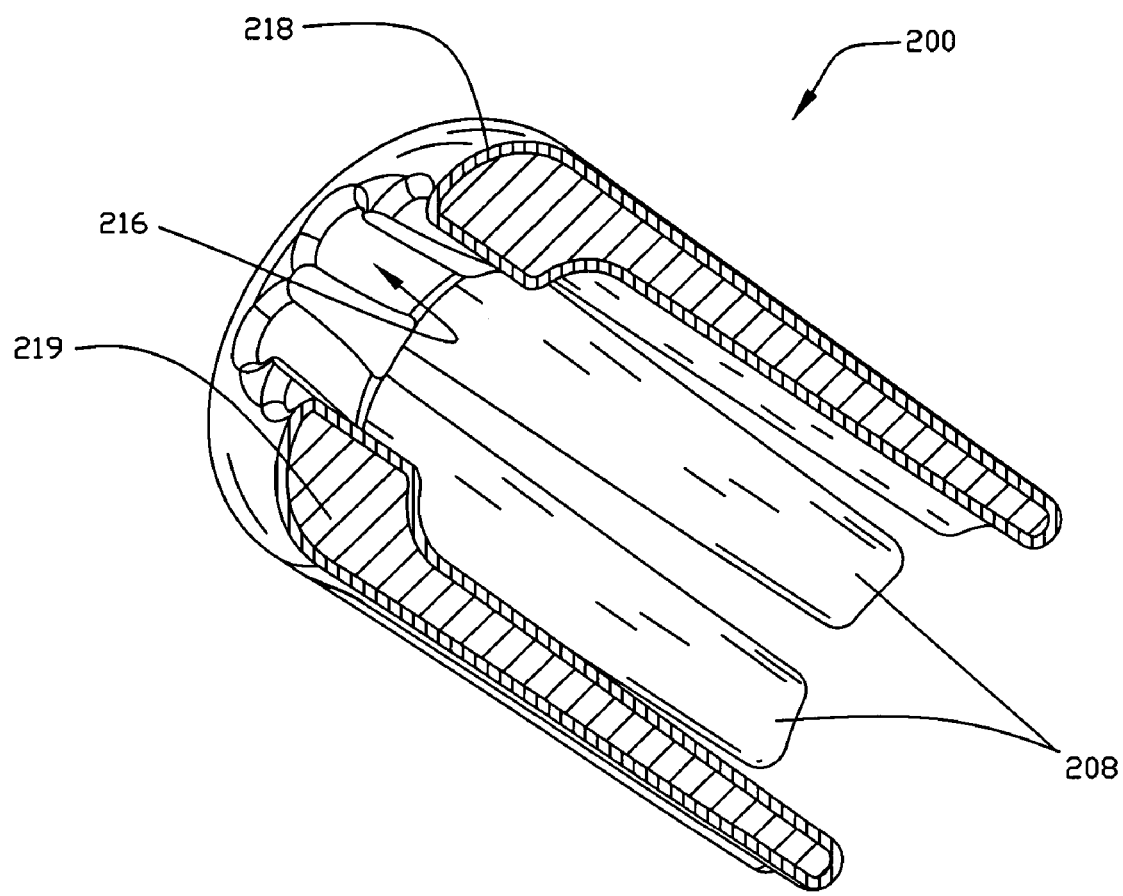
FIG. 9 is a cross-sectional side view of an adapter of the present invention.

While the adapter can consist of a skeleton having the features and abilities discussed herein, other aspects of the present invention may include a shell or coating about or on at least a portion thereof. FIG. 9 is a cross-sectional illustration of an adapter 200 of an aspect of the present invention having a portion of the coating 218 removed therefrom to show the skeleton 219 therein. The shell or coating is such that it may cover, surround, or be formed on at least a portion of the skeleton. The coating may form a shell. The shell or coating may be a thin or thick layer over or about the skeleton or portion thereof depending on the desired characteristics of the shell or coating as well as the adapter as a whole. That is, for example, the shell or coating may be used to control the size, manipulate the shape, and/or provide rigidity to the adapter. The shell or coating may also be contoured or textured so as to allow for a variety of different interface surfaces. Additionally, the use of a shell or coating enables the use of a material or materials in the skeleton which might not otherwise be as compatible with the materials of the device or component in which the adapter is located. That is, for example, a thermoplastic does not generally provide for bonding with silicone as well as, for example, silicone. Thus, if it were desired to use a ULTEM polyetheramide skeleton with a silicone tube, the bond which could be created therebetween may not be as good or as strong as if it were a silicone-silicone bond. Therefore, the use of a shell or coating can provide for a better bond as silicone can be used as the shell or a coating over all or a portion of a metallic or thermoplastic skeleton, thereby providing for a silicone-silicone bond between the shell or coating and the silicone tubing rather than a thermoplastic-silicone or metallic-silicone bond. Alternately, the shell or coating may provide for a better interface with the connector inserted in the adapter as compared with the interface which would be created between the connector and the skeleton directly. It is contemplated any suitable materials or combinations thereof may be used in the shell or coating. Exemplary materials for the shell of the present invention include silicone, PVC, and polyurethane. It is further contemplated that the desirability of a particular material or combination thereof for use in the shell or a coating may depend in part on the materials of the skeleton and/or flexible material it is bonding with or expected to. It may also be desirable to select a particular material to be part of a shell or a coating if it is know that certain glues, adhesives, or the like will be used to bond the adapter to or within a flexible tube or the like.

As suggested above, it is contemplated that the adapter as a whole or one or more of its components may be a thermoplastic. In at least one aspect of the present invention it is desirable for the thermoplastic to be bonded to a silicone or the like. An exemplary manner of doing so is to prime the thermoplastic material so that it is more receptive to the silicone or like and then to apply the silicone or the like to the adapter using an adhesive if necessary. It is further contemplated that a self-adhesive silicone may be used to facilitate bonding. It will be appreciated that the above mentioned bonding steps may be used to bond the skeleton to the shell of the adapter, the skeleton to the coating of the adapter, the skeleton to the tubing, the shell to the tubing, the coating to the tubing, as well as any other conceivable combination.

Another aspect of the present invention is directed to an adapter adapted for use with a tube, the adapter includes a skeleton having a first end, an inner surface, an outer surface, and a plurality of fingers extending opposite the first end, the fingers being flexible; and a shell, the shell contacting at least a portion of the outer surface of the skeleton. The skeleton being adapted to be received by or within the tube, and being adapted to flex so as upon sufficient insertion of a connector the adapter contacts the connector in such a manner as to create an interface between the adapter and the connector, and upon removal of the connector the fingers adopt a shape at least substantially the same as that prior to insertion of the connector. The skeleton is generally configured to urge the contours of the shell to interface with the connector when present so as to enhance retention of the connector within the adapter.

The present invention also contemplates an aspect which is directed to a relatively flexible enteral feeding tube for delivery of fluid to a patient's gastrointestinal tract. The enteral feeding tube has proximal and distal ends, and includes an enteral feeding lumen having a lumen inlet adjacent the proximal end of the tube and at least one lumen outlet adjacent the distal end of the tube. The lumen inlet is of sufficient size and is adapted to receive a feeding set connector. The lumen inlet further including an adapter and a coating, with the adapter having a first end, an inner surface, an outer surface, a plurality of fingers extending opposite the first end, where the fingers are flexible. The coating contacts at least a portion of the outer surface of the adapter and may form a shell in some aspects of the invention. The adapter is adapted to be received within or by a feeding tube and is adapted to flex so as upon insertion of the connector the adapter contacts the connector in such a manner as to create an interface between the adapter and the connector and upon removal of the connector the fingers adopt a shape at least substantially the same as that prior to insertion of the connector. As with other aspects of the present invention the adapter may be at least in part a skeleton.

A further aspect of the present invention relates to a receiving member adapted to assist with the connection of flexible tubing to a connector. The receiving member includes a first end, an inner surface, an outer surface, and a plurality of fingers extending opposite the first end. The fingers are flexible. The receiving member is adapted to receive a connector and the fingers of the receiving member are adapted to flex so that upon insertion of the connector therebetween, the fingers contact the connector in such a manner as to create an interface therewith and upon removal of the connector the fingers adopt a position at least substantially the same as that prior to insertion of the connector. As with other aspects of the present invention the receiving member is adapted to be positioned within the flexible tubing after the tubing is manufactured. Alternately, the receiving member may be at least partially encapsulated by the flexible tubing during manufacture of the tubing.

The present invention is also directed to a receiving member adapted for use with a tube, the receiving member having a first end, an inner surface, an outer surface, and at least one extension extending extending opposite the first end. The at least one extension being flexible at least in part. The receiving member is adapted to receive a connector associated with a tube or the like and the at least one extension is adapted to deform, so that upon insertion of a connector into the at least one extension the at least one extension contacts the connector in such a manner as to create an interface therebetween and upon removal of the connector the at least one extension adopts a shape at least substantially the same as that prior to insertion of the connector. Where only one extension exists it may be circumferential or substantially circumferential in shape so as to be able to surround or encompass a connector inserted thereinto. Where multiple extensions exist they may take a variety of forms as discussed above in the context of fingers.

While various patents and other reference materials have been incorporated herein by reference, to the extent there is any inconsistency between incorporated material and that of the written specification, the written specification shall control. In addition, while the invention has been described in detail with respect to specific aspects thereof, those skilled in the art, upon obtaining an understanding of the invention, may readily conceive of alterations to, variations of, and equivalents to the described aspects and the processes for making them. It is intended that the present invention include such modifications and variations as come within the scope of the appended claims and their equivalents.

I claim:

1. A receiving member provided in a flexible tube having a lumen therethrough, the lumen defining an inner surface of the flexible tube, the receiving member comprising:

a base comprising a first end formed to include an opening therethrough defined by a perimeter, the first end including a plurality of flexible fingers which extend a distance therefrom, the perimeter of the opening positioned radially inward relative to the plurality of flexible fingers, the base including an inner surface and an outer surface, the outer surface of the base positioned against the inner surface of the lumen of the flexible tube such that the flexible fingers are positioned adjacent an end of the flexible tube, the receiving member configured to couple a distal end of a connector between the plurality of flexible fingers and at least adjacent the opening in the base such that the plurality of flexible fingers move radially outward against the inner surface of the flexible tube while the inner surface of the plurality of flexible fingers flexibly holds and releaseably couples such a connector to the receiving member wherein none of the plurality of flexible fingers includes a convexity or a concavity on a surface thereof which, if present, could be positioned against a portion of a connector having a corresponding concavity or convexity to hold such a portion of a connector within the flexible fingers, and wherein the receiving member includes a skeleton, and wherein a shell covers at least a portion of the skeleton.

2. A receiving member provided in a flexible tube having a lumen therethrough, the lumen defining an inner surface of the flexible tube, the receiving member comprising:

a base comprising a first end formed to include an opening therethrough defined by a perimeter, the first end including a plurality of flexible fingers which extend a distance therefrom, the perimeter of the opening positioned radially inward relative to the plurality of flexible fingers, the base including an inner surface and an outer surface, the outer surface of the base positioned against the inner surface of the lumen of the flexible tube such that the flexible fingers are positioned adjacent an end of the flexible tube, the receiving member configured to couple a distal end of a connector between the plurality of flexible fingers and at least adjacent the opening in the base such that the plurality of flexible fingers move radially outward against the inner surface of the flexible tube while the inner surface of the plurality of flexible fingers flexibly holds and releaseably couples such a connector to the receiving member wherein none of the plurality of flexible fingers includes a convexity or a concavity on a surface thereof which, if present, could be positioned against a portion of a connector having a corresponding concavity or convexity to hold such a portion of a connector within the flexible fingers, wherein the receiving member includes a locking mechanism, and, wherein the locking mechanism comprises a recess formed in a portion of the receiving member adapted for receiving and permitting rotation of a bayonet member carried by the connector.

3. A receiving member provided in a portion of a flexible feeding tube and a feeding set, the flexible feeding tube having a lumen therethrough, the lumen defining an inner surface of the flexible feeding tube, the receiving member comprising:

a base comprising a first end formed to include an opening therethrough defined by a perimeter, the first end including a plurality of flexible fingers which extend a distance therefrom, the perimeter of the opening positioned radially inward relative to the plurality of flexible fingers, the base including an inner surface and an outer surface, the outer surface of the base positioned against the inner surface of the lumen of the flexible feeding tube such that the flexible fingers are positioned adjacent an end of the flexible feeding tube, the receiving member configured to couple a distal end of a connector associated with a feeding set, at least a portion of the distal end of the connector positioned between the plurality of flexible fingers and at least adjacent the opening in the base such that the plurality of flexible fingers move radially outward against the inner surface of the flexible feeding tube while the inner surface of the plurality of flexible fingers flexibly holds and releaseably couples at least the distal end of the connector to the receiving member wherein none of the plurality of flexible fingers includes a convexity or a concavity on a surface thereof which, if present, could be positioned against a portion of a connector having a corresponding concavity or convexity to hold such a portion of a connector within the flexible fingers, wherein the receiving member includes a locking mechanism, and wherein the locking mechanism comprises a recess formed in a portion of the receiving member adapted for receiving and permitting rotation of a bayonet member carried by the connector.

* * * * *